US012582735B2

(12) United States Patent
Schmidt-Bleker et al.

(10) Patent No.: US 12,582,735 B2
(45) Date of Patent: Mar. 24, 2026

(54) DISINFECTION METHOD COMPRISING A DISINFECTANT FORMED BY REACTION OF $H_2O_2$ AND $NO_2$ IN SITU WITH RETARDED RELEASE OF THE ACTIVE SUBSTANCE

(71) Applicant: NEBULA BIOCIDES GMBH, Greifswald (DE)

(72) Inventors: Ansgar Schmidt-Bleker, Bielefeld (DE); Jörn Winter, Greifswald (DE); Klaus-Dieter Weltmann, Ostseebad Binz (DE)

(73) Assignee: NEBULA BIOCIDES GMBH, Greifswald (DE)

( * ) Notice: Subject to any disclaimer, the term of this patent is extended or adjusted under 35 U.S.C. 154(b) by 1050 days.

(21) Appl. No.: 17/509,201

(22) Filed: Oct. 25, 2021

(65) Prior Publication Data

US 2023/0293751 A1 Sep. 21, 2023

(51) Int. Cl.
*A61L 2/18* (2006.01)
*A61L 2/186* (2026.01)

(52) U.S. Cl.
CPC ........... *A61L 2/186* (2013.01); *A61L 2202/15* (2013.01)

(58) Field of Classification Search
CPC ........... A61L 2/186; A61L 2/0088; A61L 2/18
See application file for complete search history.

(56) References Cited

U.S. PATENT DOCUMENTS

| | | | | |
|---|---|---|---|---|
| 10,499,648 | B2 * | 12/2019 | Kitano | ................... A61K 33/40 |
| 2017/0142962 | A1 * | 5/2017 | Tsai | ...................... C02F 1/4608 |
| 2021/0069361 | A1 * | 3/2021 | Schmidt-Bleker | ........ A61L 2/14 |

FOREIGN PATENT DOCUMENTS

| | | | | |
|---|---|---|---|---|
| EP | 3189857 | | 7/2017 | |
| EP | 3789045 | A1 * | 3/2021 | ............. A01N 25/34 |

OTHER PUBLICATIONS

Heaselgrave et al: "Acidified nitrite enhances hydrogen peroxide disinfection of Acanthamoeba, bacteria and fungi", Journal of Antimicrobial Chemotherapy, 2010, vol. 65, No. 23, p. 1207-1214.

* cited by examiner

*Primary Examiner* — Donald R Spamer
*Assistant Examiner* — Kayla Rose Sarantakos
(74) *Attorney, Agent, or Firm* — JMB Davis Ben-David

(57) ABSTRACT

The invention relates to a method for disinfecting surfaces comprising providing an active solution comprising the reactants $H_2O_2$ and $NO_2^-$, wherein the active solution comprises at least one stopping agent, wherein the stopping agent is a solvent having a boiling temperature below 100° C. Furthermore, the invention relates to a device for the application of this process.

16 Claims, 8 Drawing Sheets

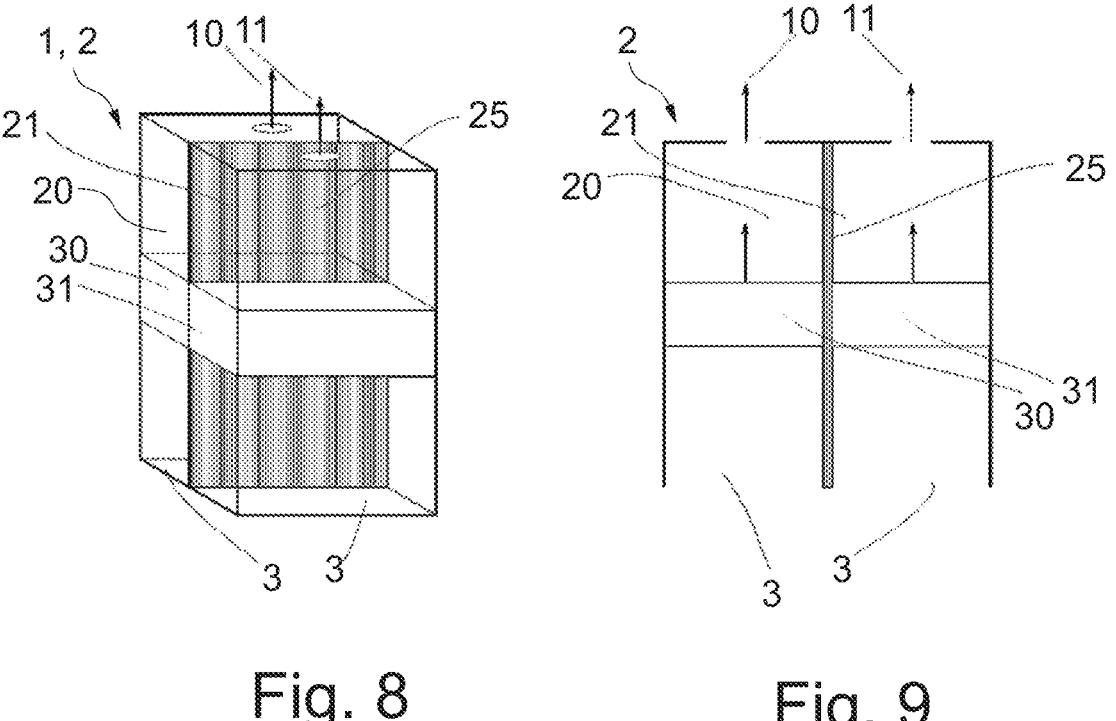
Fig. 8
Fig. 9
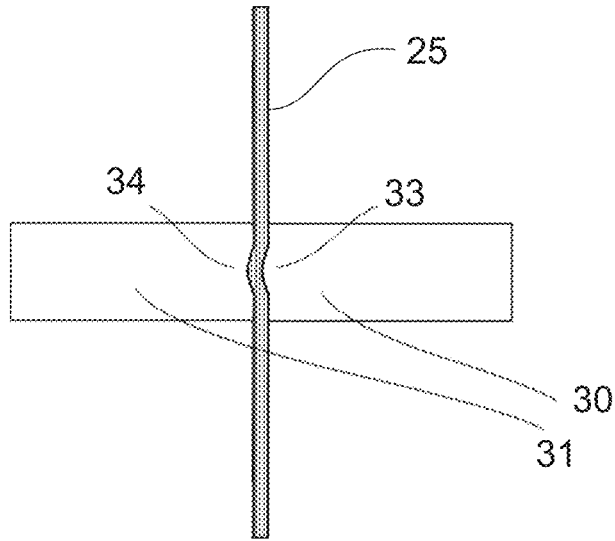
Fig. 10

DISINFECTION METHOD COMPRISING A DISINFECTANT FORMED BY REACTION OF H₂O₂ AND NO₂ IN SITU WITH RETARDED RELEASE OF THE ACTIVE SUBSTANCE

BACKGROUND OF THE INVENTION

The present invention relates to a method and a device for the disinfection of surfaces, in particular for the disinfection of body parts, in particular of hands, and/or in particular for the disinfection of wounds.

The biocidal effect of the reaction products of hydrogen peroxide ($H_2O_2$) and nitrite ($NO_2^-$) with the addition of an acid is already known in literature.

For example, by mixing two initial solutions, one of which is $H_2O_2$ and one of which is $NO_2^-$containing, a disinfecting effect can be achieved, provided that the inequation $$W = \int_{t_1}^{t_2} k \cdot [H_2O_2] \cdot [NO_2^-] dt \geq W_{min} \tag{1}$$

is satisfied. In this, W is the so-called efficacy parameter, which must be greater than $W_{min}$ to obtain an effect. The value $W_{min}$ may depend on the microorganism to be inactivated, respectively. Furthermore, k is the reaction rate of the reaction $$H_2O_2 + NO_2^- \rightarrow \text{Reaction products}, \tag{2}$$

which amongst others leads to the formation of short-lived reactive species, particularly peroxinitrite acid. Furthermore, (1) takes into account that during surface decontamination a distribution step has to be performed. This begins after the liquids have been mixed at time to and ends at time $t_1 > t_0$. Here, $t_1$ denotes the time at which the surface to be disinfected is completely wetted. The exposure time itself therefore only starts at time $t_1$ and ends at time $t_2$.

Known methods for surface decontamination have the disadvantage that the reaction rate $$R = k \cdot [H_2O_2] \cdot [NO_2], \tag{3}$$

which according to equation (1) is responsible for the biocidal effect, is highest directly after mixing the two initial solutions, since according to equation (2) the concentration of the educts is also highest then. The reaction rate is strictly monotonically decreasing for $t > t_0$. Since the exposure time does not begin until $t_1 > t_0$, as a consequence, a part of the educts has already reacted with each other before the actual disinfection process and is no longer available during the exposure time. To nevertheless ensure a sufficient effect during the exposure time, the initial reactant concentrations at time to must be selected to be significantly higher. This is disadvantageous, since high Reactant concentrations result in increased costs for disinfectant supply and also present an increased risk for the disinfection application during the distribution period due to unintended biocidal effects with harmful consequences.

Therefore, the method described subsequently is aimed at the decontamination of surfaces by means of mixtures of $NO_2^-$ and $H_2O_2$, wherein the reaction (1) is retarded by adding a suitable solvent, so that a considerably better effect can be achieved compared to the prior art. The retardation is achieved here by the retarding solvent reducing the reaction rate of the reaction (2), wherein the retarding effect decreases as soon as the concentration of the retarding solvent in the mixture is reduced, for example by evaporation of the solvent. In addition, the method according to the invention permits substantially longer processing times compared with known methods.

For the simultaneous discharge of fluids, for example, twin syringes are known in which two pistons are arranged in two cylinders and are mechanically connected to each other outside the cylinders at a common pressure element, so that when a compressive force is applied to the pressure element, the two pistons can be displaced simultaneously and can discharge fluids from the cylinders. However, this design also requires pistons of a respective length, which protrude from the cylinders before the fluids are discharged and require a corresponding amount of installation space.

This aspect is provided by a device suitable for carrying out the method according to the invention.

DESCRIPTION OF THE INVENTION

Definitions

According to the present invention, the active solution comprises a disinfecting solution applied to the surface to be disinfected. Here, the surface refers to a flat surface or a surface with irregularities and/or cavities. The active solution may contain, in addition to the disinfecting agents formed in situ, additives. Such additives comprise, but are not limited to, solvents, buffer solutions, bases, fragrances, rust inhibitors, complexing agents, dyes and/or other disinfectants and/or ozone, as well as other reaction products and reactive intermediates of the reaction between $H_2O_2$ and $NO_2^-$. According to the present invention, a dilution step comprises diluting the educts with solvents and/or additives. The dilution step precedes the mixing step or takes place simultaneously with the mixing step.

According to the present invention, a mixing step comprises mixing educts to obtain the active solution. During the mixing step, additives may additionally be mixed with the educts. The mixing step may be composed of several substeps. The mixing step starts at time $t_0 = 0$.

According to the present invention, a distribution step comprises distributing the active solution on the surface to be disinfected. Here, each point on the surface to be disinfected is wetted with active solution. The distribution step may start at the same time as the mixing step at time to or may follow it.

According to the present invention, the processing period ZA comprises the mixing step and the distribution step, i.e., the time required to mix the educts to obtain the active solution and to wet each point to be disinfected on the surface to be disinfected with active solution. The processing period begins at time $t_0 = 0$, when the educts are first brought into contact with each other, and ends at time $t_1$, when each point on the surface to be disinfected is wetted with active solution. The pH value and temperature may change within the processing period particularly if the mixing takes place before the first contact with the surface and the surface affects the pH value and/or temperature. For this reason, the pH value and temperature are time-dependent during the process.

In the context of the invention, steps relevant to the disinfection method, such as a dilution step, can also take place before the processing period, i.e. before time $t_0 = 0$.

According to the present invention, an exposure step comprises exposure of the active solution to the surface wetted with active solution for disinfection. The exposure step is described by the exposure time ZE.

According to the present invention, the exposure time ZE comprises the time period required for the active solution to achieve a sufficient disinfection effect. The exposure time begins at time $t_1$, at which every point of the surface to be disinfected is wetted with active solution, and ends at time $t_2$, at which every point of the surface wetted with active solution has been disinfected.

According to the present invention, $NO_2^-$ is a nitrite salt having the general formula $M_x NO_2$, wherein M is an alkali metal or an alkaline earth metal and x=1 or x=2. In particular, M is sodium or potassium and x=1. The nitrite salt may be present as a salt in solution or as a solid. In this case, $NO_2^-$ is in solution depending on the pH value as anion $NO_2^-$ or as acid $HNO_2$.

According to the present invention, the active ingredients, which are the reaction products of the reaction of $H_2O_2$ and $NO_2$, are formed in situ. In situ means that the active ingredients are generated only when needed.

According to the present invention, a stopping agent is a solvent which comprises a boiling temperature below 100° C. and which slows down the reaction rate of the reaction between $H_2O_2$ and $NO_2$.

DESCRIPTION

A first aspect of the invention relates to a disinfection method for surfaces comprising providing an active solution comprising educts $H_2O_2$ and $NO_2$. The method is characterized in that the active solution comprises at least one stopping agent, wherein the stopping agent is a solvent having a boiling temperature below 100° C.

After mixing the educts $H_2O_2$ and $NO_2^-$ to form an active solution, they form short-lived, reactive species, particularly peroxinitrite acid, which are responsible for the biocidal effect of the active solution. As described above, the reaction rate is highest directly after mixing, so that during the mixing process and subsequent distribution of the active solution on a surface to be disinfected, part of the educts already react with each other and are thus no longer available during the exposure period. The stopping agent reduces the reaction rate of the reaction between $H_2O_2$ and $NO_2$. The retarding effect diminishes as soon as the concentration of the retarding solvent in the mixture is reduced, for example, by evaporation of the solvent. Thus, the method according to the invention allows longer processing times.

In some embodiments, the stopping agent is selected from an alcohol, a ketone, and an ester.

In some embodiments, the stopping agent is selected from methanol, ethanol, isopropanol, acetone, ethyl acetate, and n-propanol.

In some embodiments, the stopping agent is selected from ethanol, isopropanol, and acetone.

In some embodiments, the active solution is obtained by mixing the educts $H_2O_2$ and $NO_2^-$ and the stopping agent at time to.

Before mixing the educts, they can be present separately or partially mixed. For example, an $H_2O_2$ solution, an $NO_2^-$ solution and the solvent (stopping agent) can be present separately. Alternatively, the stopping agent may be present in either the $H_2O_2$ solution or the $NO_2^-$ solution. It is also possible that a part of the stopping agent is present in the $H_2O_2$ solution and another part of the stopping agent is present in the $NO_2^-$ solution.

In some embodiments, the active solution is distributed on a surface to be disinfected until complete wetting at time $t_1$.

In some embodiments, the time period between $t_0$ and $t_1$ is at least 5 seconds.

In some embodiments, the time period between $t_0$ and $t_1$ is at least 10 seconds.

In some embodiments, the time period between $t_0$ and $t_1$ is at least 15 seconds.

Particularly in a medical context, hygiene regulations stipulate a prescribed distribution time for the active solution. Typically, active solutions for hand disinfection are distributed for at least 30 seconds.

In some embodiments, the active solution acts until time $t_2$ to obtain a disinfected surface.

In some embodiments, the minimum concentration of stopping agent in the active solution at time to is at least 2.5% (v/v) and/or the maximum concentration of stopping agent in the active solution is <90% (v/v), particularly <60% (v/v), further particularly <40% (v/v).

In some embodiments, the minimum concentration of stopping agent in the active solution at time to is at least 2.5% (v/v).

Time to is the time of mixing, when the educts first come into contact with each other.

In some embodiments, the maximum concentration of stopping agent in the active solution is <90% (v/V).

In some embodiments, the maximum concentration of stopping agent in the active solution is <60% (v/v).

In some embodiments, the maximum concentration of stopping agent in the active solution is <40% (v/V).

After the distribution time, the reaction time starts at time $t_1$. In order to obtain at least 20% more educts in the active solution with stopping agent compared to an active solution without stopping agent, the condition from equation (100) must be fulfilled.

$$\frac{c_{t_1}^{min}(x)}{c_{t_1}^{min}(0)} > 1, 2, \tag{100}$$

wherein $$c_{t_1}^{min}(x) = \min([H_2O_2] \ (x, t = t_1), [NO_2^-](x, t = t_1)),$$

wherein x is the concentration of the stopping agent in volume percent with respect to the volume of the active solution at time $t=t_0$, $[H_2O_2](x, t)$ describes the concentration of $H_2O_2$ at time t, $[NO_2](x, t)$ describes the concentration $NO_2^-$ at time t.

$$c_{t_1}^{min}(0)$$

refers to an active solution without stopping agent.

$$c_{t_1}^{min}$$

corresponds to the maximum achievable efficacy $$W = \int_{t_1}^{\infty} k \cdot [H_2O_2] \cdot [NO_2^-] dt,$$

wherein k denotes the rate constant of the reaction between $H_2O_2$ and $NO_2$, i.e. the educt whose concentration is lowest determines how much biocidal action is still maximally possible.

In some embodiments, the pH value of the active solution at time to is between 1, and 7.

In some embodiments, the pH value of the active solution at time to is between 2 and 6.

In some embodiments, the pH value of the active solution at time to is between 3 and 5.

In the event that the pH value cannot be readily determined, the following definition of the pH value applies in the context of the present invention: The pH value of a solution with x>0 (i.e. with a solvent concentration (stopping agent) >0%) is to be defined as the pH value measured with a pH electrode when the volume fraction of the solvent (x) has been replaced by water.

In some embodiments, the initial concentration $[H_2O_2]_0$ at time to is between 1 mM and 1000 mM.

In some embodiments, the initial concentration $[H_2O_2]_0$ at time to is between 10 mM and 500 mM.

In some embodiments, the initial concentration $[H_2O_2]_0$ at time to is between 15 mM and 300 mM.

In some embodiments, the initial concentration $[NO_2]_0$ at time to is between 1 mM and 1000 mM.

In some embodiments, the initial concentration $[NO_2]_0$ at time to is between 10 mM and 500 mM.

In some embodiments, the initial concentration $[NO_2]_0$ at time to is between 15 mM and 300 mM.

The disinfection process of the present invention comprising at least the educts $H_2O_2$ and $NO_2^-$ consists of several substeps comprising at least:

a mixing step wherein the educts are mixed to obtain an active solution;

a distribution step in which the active solution is distributed on a surface to be disinfected, wherein the mixing step and the distribution step take place in a processing period ZA starting at time $t_0$ when the educts are first brought into contact with each other and ending at time $t_1$, when each point on the surface to be disinfected is wetted with active solution, wherein to is equal to 0 and $t_1$ is larger than $t_0$, and subsequently an exposure step in which the distributed active solution acts on the surface contacted with active solution over an exposure period ZE, which begins at time $t_1$ and ends after the time period ZE at time $t_2$, wherein $t_2$ denotes the time at which each point on the surface contacted with active solution is wetted with active solution for a sufficient time to obtain a disinfecting effect, and wherein $t_2$ is greater than $t_1$, the time-integrated reaction rate W over the exposure period ZE is represented by the integral $$W = \int_{t_1}^{t_2} k_1 \cdot [H_2O_2] \cdot [NO_2^-] dt \geq 10 \; mM, \qquad (5)$$

wherein $t_1$ and $t_2$ are as defined above, and, wherein $[H_2O_2]$ and $[NO_2]$ denote the concentrations of the educts during the exposure period $Z_E$, and wherein $k_1$ denotes the pH-dependent rate constant of the reaction between $H_2O_2$ and $NO_2^-$ or $HNO_2$, and wherein the pH-value and the temperature may comprise a time dependence, and in some embodiments, the maximum $NO_2^-$ concentration at time to of the mixing step is 300 mM.

In some embodiments, $t_2$ does not exceed 3 minutes.

In some embodiments, the pH value of the active solution prior to contact with the surface to be disinfected is in the range of 2.1≤pH<6.8

The pH-dependent rate constant $k_1$ can be calculated as follows:

$$k_1 = k_4 \frac{[H_3O^+]^2}{\left(K_{S,H_3O_2^+} + [H_3O^+]\right)\left(K_{S,HNO_2} + [H_3O^+]\right)} \; with \qquad (6)$$

$$k_4 = 3,56 \cdot 10^{14} \exp\left(-\frac{E_A}{RT}\right) M^{-1} s^{-1} \qquad (7)$$

$$K_{S,HNO_2} = 5,13 \times 10^{-4} \qquad (8)$$

$$K_{S,H_3O_2^+} = 2 \times 10^{-2} \qquad (9)$$

and the unitless quantity $$[H_3O^+] = 10^{-PH} \qquad (10)$$

with the effective activation energy $E_A = 70$ KJ/mol and the temperature T. At 20° C., $k_4$ is 120 $M^{-1}s^{-1}$.

The time-dependent concentrations of the educts $NO_2^-$ and $H_2O_2$ can be calculated during the exposure time using the following equations:

$$[NO_2^-] = \frac{A}{k_1}, \qquad (11)$$

$$[H_2O_2] = \frac{A+D}{k_1 + rk_1}, \; with \qquad (12)$$

$$A = -\frac{D}{1 - \exp(D(t-C))} \qquad (13)$$

$$C = -\frac{\ln\left(\frac{D}{[NO_2^-]_0 \cdot k_1} + 1\right)}{D} \; and \qquad (14)$$

$$D = [H_2O_2]_0 \cdot (k_1 + rk_1) - [NO_2^-]_0 \cdot k_1, \qquad (15)$$

with $k_1$, $k_4$, $K_{S,HNO2}$, $K_{S,H3O+2}$ und $[H_3O^+]$ as described above.

$[H_2O_2]_0$ and $[NO_2]_0$ denote the initial concentrations at the time of the mixing step of $H_2O_2$ and $NO_2$" in the active solution. These are given by the educt concentrations and the type of mixing or dilution. For example, in the case of an educt concentration of 200 mM $H_2O_2$ in educt solution 1 and 200 mM $NO_2^-$ in educt solution 2 and a mixing ratio of 1:1, initial concentrations of $[H_2O_2] = [NO_2]_0 = 100$ mM are obtained.

In addition $$r = 0,11 \qquad (16)$$

wherein r is an outgassing coefficient describing the formation of NOx from $NO_2^-$ and is described in more detail below.

As the starting substances ($NO_2^-$ and $H_2O_2$) are converted over time, the effective reaction rate of the reaction between $H_2O_2$ and $NO_2^-$ steadily decreases. Due to the short half-life of the reaction products, they are not accumulated and thus the instantaneous reaction rate of $H_2O_2$ and $NO_2^-$ is decisive for the effectiveness of the active solution at a given time during the exposure period. For the use of the active solution as a disinfectant, it is necessary that the efficacy is given for a defined minimum duration of action. Therefore, the time-integrated reaction rate W must not fall below a minimum value. The heuristic equation (5) allows applicable concentrations of $H_2O_2$ and $NO_2^-$ and a respective pH value to be selected for decontamination applications at a given process temperature.

In contrast to vegetative bacteria, bacterial spores and non-enveloped viruses cannot be inactivated with alcohol-based agents or only after an insufficiently long time. At a reaction rate $W \geq 10$ mM, not only vegetative bacteria but also bacterial spores are inactivated.

In an embodiment, the time-integrated reaction rate W of the reaction between $H_2O_2$ and $NO_2^-$ is greater than or equal to 17.

At a reaction rate $W \geq 17$ mM, not only vegetative bacteria and bacterial spores but also non-enveloped viruses are inactivated.

In an embodiment directed exclusively to vegetative bacteria, $W=0.3$, particularly 0.5.

A higher time-integrated reaction rate W increases the disinfecting effect on the surface contacted with active solution.

The processing period ZA comprises the mixing step and the distribution step, wherein the distribution step may start at the same time as the mixing step at time $t_0=0$, or may follow it. The processing period starts at $t_0=0$.

Furthermore, relevant steps can also take place before the processing period, i.e. before the time $t_0=0$, such as a dilution step. However, these steps are not relevant for the time interval for calculating the time-integrated reaction rate and can therefore be before $t_0=0$.

The processing period must be sufficiently long to wet every point of the surface to be disinfected with active solution. At the same time, however, the processing time should not be too long so that after distribution of the active solution on the surface to be disinfected, sufficient reactive active solution is still present to achieve a disinfecting effect and the necessary portion of stopping agent is relatively low at the same time.

In some embodiments, the processing period ending at time $t_1$ is selected from a range of $0 < t_1 75$ s, in particular is selected from the range $0 < t_1 \leq 30$ s, in particular is selected from a range $0 < t_1 \leq 15$ s, in particular is selected from a range $0 < t_1 \leq 2$ s.

In some embodiments, the exposure time begins after 2 s.

In some embodiments, the exposure time begins after 15 s.

In some embodiments, the exposure time begins after 30 s.

In some embodiments, the exposure time begins after 75 s.

In some embodiments, a longer processing period is required, ending at time $t_1$, wherein this is selected from a range of $15 < t_1 \leq 75$ s, particularly selected from a range of $30 < t_1 \leq 75$ s, particularly selected from a range of $50 < t_1 \leq 75$ s.

In some embodiments, a shorter processing period is required, ending at time $t_1$, wherein this is selected from a range of $0 < t_1 \$30$ s, in particular selected from the range $0 < t_1 \leq 15$ s, in particular selected from a range $0 < t_1 \leq 2$ s.

In some embodiments, a processing period ending at time $t_1$ is required, wherein this is selected from a region of $2 < t_1 \leq 75$ s, in particular selected from the region $2 < t_1 \leq 30$ s, in particular selected from a region $2 < t_1 \leq 15$ s.

Furthermore, the time range (the sum of ZA and ZE), particularly for applications in hand disinfection, should be sufficiently short to achieve the necessary disinfecting effect in a region that is still appropriate. An excessively long time period, such as more than 10 minutes, is neither practicable nor sensible to use for hand disinfection, even in the clinical region.

The mixing of educts $H_2O_2$ and $NO_2^-$ to produce the active solution can take place before contact with the surface to be disinfected, or take place directly on the surface to be disinfected. The mixing step can take place without external influence by diffusion and convection, be supported by mechanical distribution, or be integrated in a spraying process in which the educts are sprayed together onto the surface to be disinfected.

Furthermore, the pH value plays a decisive role in the disinfection process according to the invention.

In some embodiments, the pH value of the active solution on the surface contacted with active solution is located in the range of $2.1 \$ pH \leq 6.8$, particularly in a range of $2.5 \leq pH \leq 5$, and particularly in a range of $3.3 \leq pH \leq 4.7$.

The reaction rate of the reaction between $H_2O_2$ and $NO_2^-$ depends on the pH value of the solution according to (6). With decreasing pH values, i.e. with increasing concentration of $H_3O^+$, the reaction rate k, increases. At low pH values, therefore, the disinfecting effect of the active solution is higher, but low pH values do not allow a sufficiently long processing and exposure period due to the high reaction rate of $H_2O_2$ and $NO_2^-$ in combination with the short-lived nature of the reaction products formed. At higher pH values, the reaction rate of $H_2O_2$ and $NO_2^-$ decreases significantly, which, however, also reduces the disinfecting effect of the active solution.

In contrast to decontamination in suspensions, it was found that acidification can lead to a significant deterioration of the effect when decontaminating surfaces. This results from the need for the liquid to be applied and/or distributed on the surface in a distribution step and, in the case of structured and porous surfaces, to penetrate the surface by diffusion. The active solution must not lose its disinfecting effect during this time, however, this is caused by a pH value that is too low. In this case, the educts are degraded too quickly before they can exert their antimicrobial effect at any point on the surface. This problem is solved by the present invention for an active solution of at least $NO_2^-$ and $H_2O_2$ by identifying a range of pH values in which use as a surface disinfection agent is possible.

Many surfaces themselves have a pH-regulating property, in particular a buffering effect, such as the skin surface. The pH value which is decisive for the method of the present invention is therefore the pH value which results on the surface wetted with active solution. Such buffering surfaces and their buffering effect are known to the skilled person.

In an embodiment of the present invention, the disinfection method is to be used for disinfection of a surface strongly buffering the pH value, in particular skin, wounds or other organic surfaces, wherein a suitable pH value on the surface results from the fact that the pH value of the active solution prior to contact with the surface to be disinfected is in the range of 2.1 to 4.5, in particular in a range of 2.1 to 3.6, in particular in a range of 2.1 to 3.2.

This pH value is increased by 0.2 to 1.7, in particular by 0.2 to 0.8, by contact with the buffering surface, depending on the surface properties.

As a result, the pH value of the active solution is lower than the pH value of the active solution on the surface to be disinfected. Due to this property, the educts react quickly outside the surface to be disinfected and do not accumulate in the environment. On the surface to be disinfected, however, particularly on the surface of a body part, particularly a hand, the reaction between $H_2O_2$ and $NO_2^-$ due to the buffering effect of the surface proceeds somewhat more slowly, allowing the disinfecting effect to unfold. Thus, the disinfecting effect remains effective for a sufficiently long time on the intended surface; on surfaces not intended for this purpose, rapid degradation of the educts takes place and thus no accumulation occurs.

In an embodiment, the initial quantities of the educts are identical, particularly in applications where outgassing of NOx is negligible, thus $NO_2^-$ and $H_2O_2$ are completely converted. Thus, no biocidal active substances are released into the environment.

In an embodiment, the efficiency E=W/Wmax of the method at process-dependent predetermined times $t_1$ and $t_2$ is at least 10%, particularly at least 20%, particularly at least 30%, wherein $$W_{max}=min([H_2O_2]_0, [NO_2^-]_0)(exp(-Gt_1)-exp(-Gt_2)) \quad (17)$$

with $$G = ln\left(\frac{t_2}{t_1}\right)\bigg/(t_2 - t_1)$$

denoting the $t_1$ maximum achievable efficacy parameter and min $([H_2O_2]_0, [NO_2^-]_0)$ denoting the minimum concentration selected from the initial concentrations $[H_2O_2]0$ and $[NO_2^-]_0$. This ensures that the educts used are efficient by reasonable selection of the selectable process parameters pH value, temperature and initial concentrations of the educts.

In an embodiment, the initial quantities of educts differ from each other by less than 10%, in particular the initial quantity of $NO_2^-$is 2% to 10% higher than the initial quantity of $H_2O_2$. The exact value is to be determined for a given application, i.e. for a given surface and amount of liquid. In this case, only nitrate and water are formed as stable end products, while $NO_2^-$ and $H_2O_2$ are completely converted. As a result, no biocidal active substances are released into the environment. The disinfection method according to the invention is thus particularly environmentally friendly.

A slightly higher initial amount of $NO_2^-$compared to $H_2O_2$ is helpful to prevent the loss of effective $NO_2^-$due to outgassing of NOx.

The outgassing of NOx is significantly greater for surface disinfection due to the larger surface area than for disinfection that takes place in solution or suspension. When the active solution is distributed over a surface, only a thin film of liquid is formed, during which large portions of the $NO_2^-$used can be released as gaseous nitrogen oxides (NOx). One of the consequences of this is that up to 10% of the $NO_2^-$introduced into the liquid is outgassed in the form of NO (g) or particularly $NO_2^-(g)$. The outgassing leads to an accelerated degradation of $NO_2^-$in an active solution of $H_2O_2$ and $NO_2^-$on surfaces, compared to an identically prepared active solution in suspension. The outgassing influences the reaction kinetics and should also be kept low for health reasons.

The NOx emissions are to be attributed to two basic processes: On the one hand, the use of an acid to adjust the pH value can directly cause NOx outgassing, for example the process:

$$HNO_2+HNO_2\rightarrow NO+NO_2+H_2O\rightarrow NO(g)+NO_2^-(g)+H_2O. \quad (18)$$

shown in FIG. 1.

The presence of $H_2O_2$ is not required for process (18). On the other hand, the formation of ONOOH, which requires the presence of $H_2O_2$, can be achieved by the reaction (19)

$$ONOOH\rightarrow NO_2+OH \quad (19)$$

by subsequent outgassing of $NO_2^-$contributing to NOx emissions.

The outgassing of NOx has been studied in experiments and computer simulations. In an embodiment of the present invention, the outgassing is expressed as the outgassing rate by the equation $$R_{degas}=R_1\times r, \quad (20)$$

which can be assumed proportional to the effective annihilation rate $R_1$ of $NO_2^-$ and $H_2O_2$ by reaction (1), and contributes to the annihilation of $NO_2^-$corresponding to the equation $$\frac{d[NO_2^-]}{dt} = -R_1 - R_{degas} = -k_1[H_2O_2][NO_2^-]\times(1+r). \quad (21)$$

Here, r denotes a portion related to R 1, which leads to the outgassing of $NO_2^-$in the form of $NO_x$. This form results from the reaction $$ONOOH\rightarrow NO_2+OH \quad (22)$$

making the essential contribution to outgassing during surface decontamination. While r in suspension experiments is usually negligibly small, approximately in the range of r≤0.01, r in surface decontamination can adopt values in the range of r≤0.11. The specific value depends on the application in question, in particular on the layer thickness of the liquid film. Thus, the outgassing that occurs influences the reaction kinetics of the reaction of $H_2O_2$ and $NO_2^-$in the case of surface disinfection, which would be negligible in the case of disinfection in suspension.

One possible way to delimit the amount of outgassing $NO_x$, is to delimit the initial concentration of $NO_2^-$.

Thus, in some embodiments, a maximum initial concentration of $NO_2^-$at time to does not exceed a concentration of 300 mM, particularly 200 mM, particularly 100 mM.

The disinfection method according to the invention can be used for the disinfection of surfaces. The disinfection method according to the invention can be used in particular for disinfection of skin and/or for disinfection of wounds.

The disinfection method of the present invention may further be employed for decontaminating medical devices, particularly thermolabile medical devices such as endoscope tubing, as well as containers and tubs.

The disinfection method of the present invention may further be used to decontaminate seeds, crops, animal products, food, packaging as well as beverage containers or beverage lines.

In an embodiment of the disinfection method according to the invention, acid buffers or acid buffer solutions can be added to the educts and/or the active solution. For example, citrate buffer, acetic acid-acetate buffer, phosphate-citrate buffer, phosphate buffer or citrate buffer can be used as buffers. Buffer solutions containing citrate are particularly suitable because of their pleasant odor.

In an embodiment of the disinfection method according to the invention, additives may be added to the educts before and/or during the mixing step. Conceivable additives comprise, among others, solvents, bases, fragrances, dyes and/or further disinfectants, and/or ozone.

Furthermore, suspensions with non-water-soluble substances can be produced, in particular by admixing fats and surfactants.

In a further embodiment, one or more plasma sources may be used to produce one or more of the educts.

Thus, it would be possible to produce the educts $H_2O_2$ and $NO_2^-$ from air and water using electricity. The state of the art discloses plasma methods sufficiently for the skilled person to select a respective plasma.

In a further embodiment of the present invention, the plasma additionally produces ozone, which may be part of the active solution.

The disinfection method for surfaces, which is the subject of this invention, is characterized in that it has a sporicidal effect. There is no approved disinfectant in Germany for the disinfection of skin that also has a disinfecting effect against bacterial spores. Furthermore, the method according to the invention has a low odor and is advantageous compared to conventional disinfection methods for the disinfection of skin, because it does not dry out the skin.

Another aspect of the invention provides a device for simultaneous delivery of at least two volume flows of $H_2O_2$ and $NO_2^-$ solutions, in particular of at least two volume flows of the same size, comprising at least two reservoirs for receiving $H_2O_2$ and for receiving $NO_2$, and, arranged in a respective reservoir, a displaceable piston for conveying a fluid from the respective reservoir, wherein the pistons are coupled to one another via a force-transmitting apparatus in such a way that they can be displaced synchronously parallel to one another, so that the fluids can be discharged from the reservoirs at the same time, in particular with the same volume flows.

The stopping agent can either be included in one or both of the $H_2O_2$ and $NO_2$ volume flows or added via a third volume flow.

The pistons can be displaced simultaneously at the same speed. This means that the pistons also have the same acceleration behavior, so that completely identical movement sequences on two movement paths arranged parallel to each other can be realized with them, so that the fluids can be discharged simultaneously with a fixed mixing ratio.

In particular, the two reservoirs may be arranged in a common cartridge.

In an embodiment, the device for simultaneous delivery of at least two volume flows of $H_2O_2$ and $NO_2^-$ is characterized in that the two reservoirs are separated from each other by at least one common partition wall, wherein this partition wall comprises a lower bending strength than the sides of the pistons sliding on the partition wall and wherein a first piston comprises a projection projecting in the direction of a second piston and the second piston comprises a recess which is essentially complementary with respect to the shape and size of the projection, so that when one piston is displaced, the respective other piston is entrained in the recess whilst deforming the partition wall via indirect mechanical engagement of the projection.

Mechanical engagement takes place only indirectly, since a region of the sectionally deformed partition wall, designed in particular as a diaphragm, continues to be arranged between the projection and the recess.

In an embodiment, the device for simultaneous delivery of at least two volume flows of $H_2O_2$ and $NO_2^-$ is characterized in that the reservoirs are separated from one another by at least one common partition wall, wherein the pistons are connected via at least one connecting member which is arranged to cut the partition wall located therebetween at least sectionwise upon displacement of the pistons.

For this purpose, the connecting member is preferably equipped with a wedge segment or a cutting edge or blade with which it is possible to cut into or slice the partition wall, which is designed in particular as a diaphragm, even when little force is applied to the pistons.

In an embodiment, the connecting member with the cutting edge is located on the side of the pistons opposite the respective outlets from the reservoirs with respect to the axis of movement of the piston unit realized by means of the connecting member.

In an embodiment, the device for simultaneous delivery of at least two volume flows of $H_2O_2$ and $NO_2^-$ is characterized in that each reservoir comprises an outlet, wherein a fluid conduit is connected to a respective outlet, which is fluidically connected to a mixing unit for mixing the fluids from the reservoirs.

Such a mixing unit can be, for example, a so-called T-piece, in which the fluids from two reservoirs are combined.

In a further advantageous embodiment of the device according to the invention, it is provided that a check valve is arranged in the flow path between a respective outlet and the mixing unit, respectively, for preventing mixed fluid from flowing back into the reservoirs.

In an embodiment, the device for simultaneous delivery of at least two volumetric flows of $H_2O_2$ and $NO_2^-$ is characterized in that a first pump is fluidically connected to the mixing unit for generating a negative pressure and thus for conveying the mixture of fluids from the mixing unit.

In an embodiment, the device for simultaneous delivery of at least two volume flows of $H_2O_2$ and $NO_2^-$ is characterized in that the device comprises an outlet device, in particular a nozzle, with which the fluids can be discharged as a mixture in liquid form or also as a spray mist.

In an embodiment, the device for simultaneous delivery of at least two volume flows of $H_2O_2$ and $NO_2^-$ is characterized in that the force transmission apparatus comprises one force transmission element for each piston, with which a force can be applied to one piston respectively for the purpose of displacing the piston, wherein the two force transmission elements are mechanically coupled to one another.

In particular, this mechanical coupling can be implemented on or by means of a thrust apparatus, with which a force can be exerted respectively on a respective force transmission element, which in turn transmits this force to the respective piston.

In an embodiment, the device for simultaneous delivery of at least two volumetric flows of $H_2O_2$ and $NO_2^-$ is characterized in that the force transmission apparatus is assigned to at least one piston and comprises, fluidically coupled to the latter, in particular delimited by the latter at least in certain regions on one side, a pressure chamber to which a second pump for generating an overpressure is fluidically connected, so that the respective piston is displaced when the second pump is actuated and an overpressure is generated.

This means that on its side opposite the fluid to be discharged, the piston is fluidically connected to the second pump for generating an overpressure, so that when the overpressure is generated on the side of the piston facing away, from the fluid, this piston is displaced and conveys the fluid out of the reservoir assigned to it accordingly.

Several pistons can be assigned to a common pressure chamber.

In an embodiment, the device for simultaneous delivery of at least two volume flows of $H_2O_2$ and $NO_2^-$ is characterized in that the device comprises three reservoirs, wherein a displaceable third piston is arranged in the third reservoir for delivery of a fluid from the third reservoir, wherein the three pistons are coupled to each other via a force transmission apparatus such that they are synchronously displaceable parallel to each other, so that the fluids can be delivered from the reservoirs with equal volume flows.

In an embodiment, the device for simultaneously delivering at least two volume flows of $H_2O_2$ and $NO_2^-$ is characterized in that at least a first reservoir is neighbouring on at least two sides of at least a further reservoir, wherein in the further reservoir the fluid comprises a lower translucency than the fluid in the first reservoir for the purpose of reducing light irradiation into the fluid in the first reservoir.

In a specific embodiment, it is provided that the first reservoir is completely surrounded by two further reservoirs.

In a further aspect of the invention, a method is provided for simultaneously delivering at least two volume flows of $H_2O_2$ and $NO_2$", in particular at least two volume flows of the same size, wherein at least two reservoirs comprising $H_2O_2$ and $NO_2^-$ are provided, and in a respective reservoir a piston is displaced for delivering a respective fluid from the respective reservoir, wherein the pistons are coupled to one another via a force transmission apparatus in such a way that they are displaced synchronously parallel to one another, so that the fluids are discharged from the reservoirs at the same time, in particular with equal volume flows.

In embodiments with only two reservoirs, the stopping agent is in one or both of the volume flows of $H_2O_2$ and $NO_2$. In the presence of a third reservoir, the stopping agent can be added alternatively or additionally via this reservoir.

Reference Listing:
1 Device
2 Cartridge
3 Opening
10 Volume flow to the first reservoir
11 Volume flow to the second reservoir
20 First reservoir
21 Second reservoir
22 Third reservoir
23 Outer reservoir
24 Inner reservoir
25 Partition wall
26 Bending zone
30 First piston
31 Second piston
32 Third piston
33 Projection
34 Recess
35 Thrust of the pistons
36 Force transmission elements
50 Connecting member
51 Blade
60 First pump
61 Check valves
62 Mixing unit
63 Nozzle
64 Pressure chamber
65 Second pump

BRIEF DESCRIPTION OF THE FIGURES

FIG. 8 shows a device according to the invention in perspective view,

FIG. 9 shows a sectional view of the device shown in FIG. 1,

FIG. 10 shows a part of the sectional view in FIG. 2,

Figure 1:
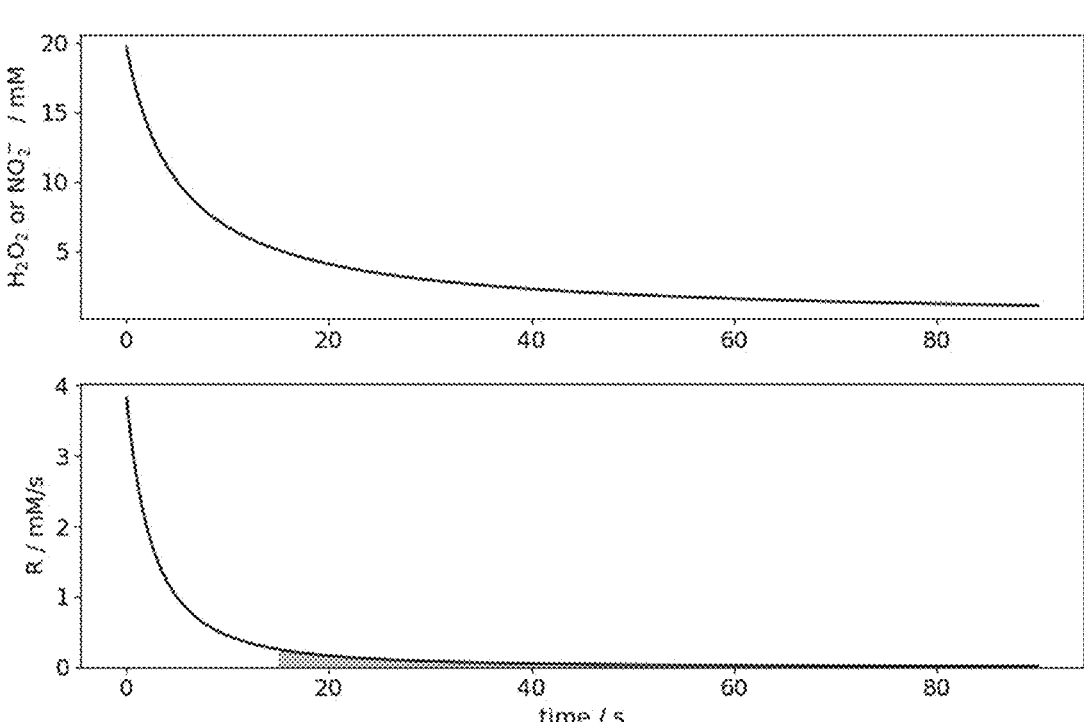
FIG. 1 shows the concentration curve (top) and the reaction rate according to equation (3) (bottom) with $[H_2O_2]_0=[NO_2^-]=20$ mM as well as a pH value of 3.3 and a temperature of 37° C. The filled region illustrates the integral over the reaction time from $t_1=15$ s to $t_2=75$ s.

Detailed description of FIGS. 8 to 19

A cartridge 2 as part of the device 1 according to the invention is shown in FIGS. 8 and 9 as an example with two reservoirs 20, 21. FIG. 8 shows a cartridge 2 which has two reservoirs 20, 21 which are separated from each other by a partition wall 25 in the form of a membrane. The device 1 has two openings 3 into which the respective fluids can be introduced. The pistons 30,31 are displaceable in the reservoirs 20,21 along a direction of movement, wherein they can only be moved in the thrust direction, i.e. tangentially to the partition wall 25. The movement of the pistons 30,31 takes place to reduce the volume of a respective reservoir 20,21 so that fluid received in a respective reservoir 20,21 is expelled.

The movement of the two pistons 30,31 cannot occur independently of each other in this case. The device 1 is designed in such a way that the pistons 31,31 can only move synchronously so that they always generate a respective volume flow 10,11 of fluid to the same extent. In particular, both reservoirs 20,21 can comprise the same size and both pistons 30,31 can comprise the same cross-section, so that the two volume flows 10,11 are also equal.

FIG. 10 shows the pistons 30, 31 and a partition wall 25 formed as a membrane of the device 30, 31 according to the invention, in which the pistons 30, 31 are indirectly mechanically coupled in that a first piston 30 has a projection 33 and a second, neighbouring piston 31 has a recess 34 of complementary shape and size, so that the projection 33 engages indirectly in the recess 34 and in this way, when one piston 30, 31 moves, the other piston 30, 31 is carried along. The partition wall 25, formed as a membrane, is here designed to be so little bend-resistant or flexible that it can form a respective bending zone 26 in the region of the engagement of the projection 33 in the recess 34.

Figures 11, 12, 13:
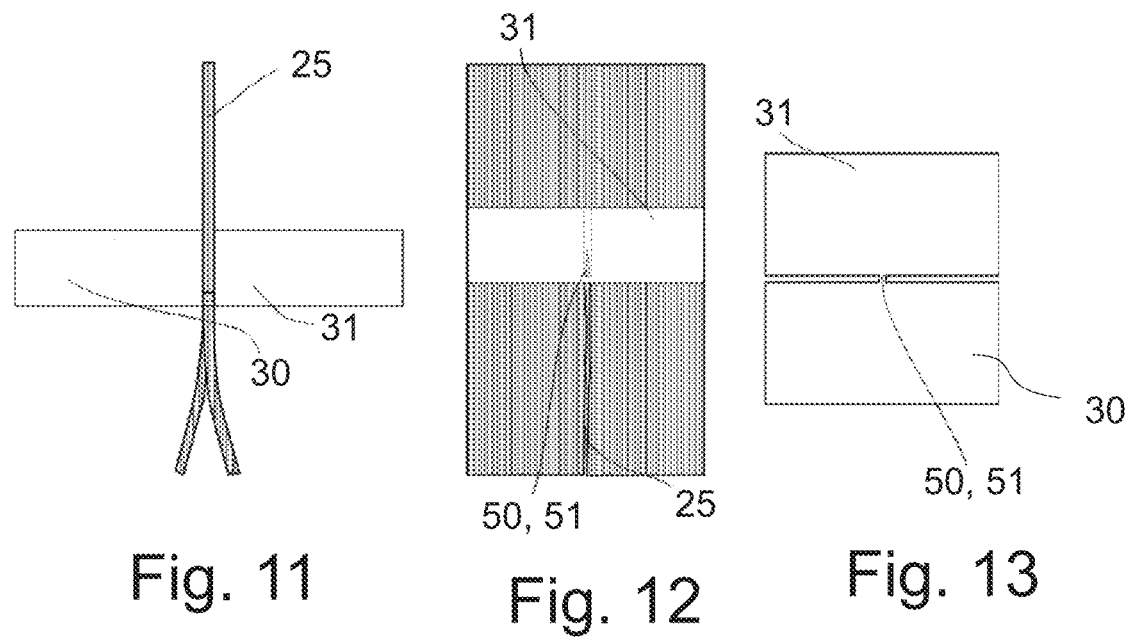
FIG. 11 shows a part of the sectional view from FIG. 2 during a cutting process.
FIG. 12 shows the cutting process in another side view.
FIG. 13 shows the two pistons with the connecting member in top view.

FIGS. 11, 12 and 13 show pistons 30, 31 and partition 25 of an embodiment of the device 1 in which the pistons 30, 31 are mechanically coupled by means of a connecting member 50 so that they can only be displaced together. The connecting member 50 is designed as a blade 51. In particular, the pistons 30, 31 and the connecting member 50 can be made of the same material, so that a single, coherent piston unit results.

Figure 14:
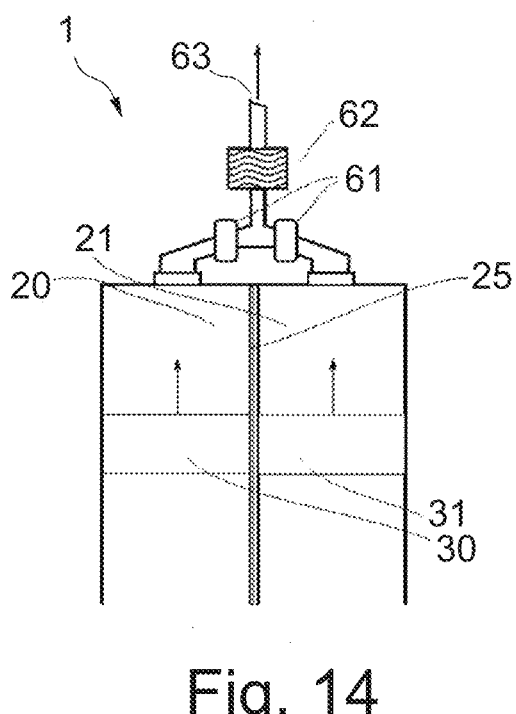
FIG. 14 shows a part of the device according to the invention with mixing unit and first pump.

FIG. 14 shows how the fluid can be extracted by a first pump 60, which exerts a suction on the fluids in the reservoirs 20,21. Here, uncontrolled mixing of the two fluids in the reservoirs 20,21 is prevented by two check valves 61. The mixing of the two fluids takes place downstream of the valves 61, in the so-called dead volume, which is realized by a mixing unit 62, located upstream of the first pump 60. In contrast to the extraction of the fluids with two individual pumps, this design has the advantage that in the event of a malfunction of the first pump 60, no fluid can be discharged, so that the malfunction is directly apparent to the user.

The mixture of fluids may be dispensed, nebulized, or sprayed from the nozzle 63 for further use as a liquid.

Figure 15:
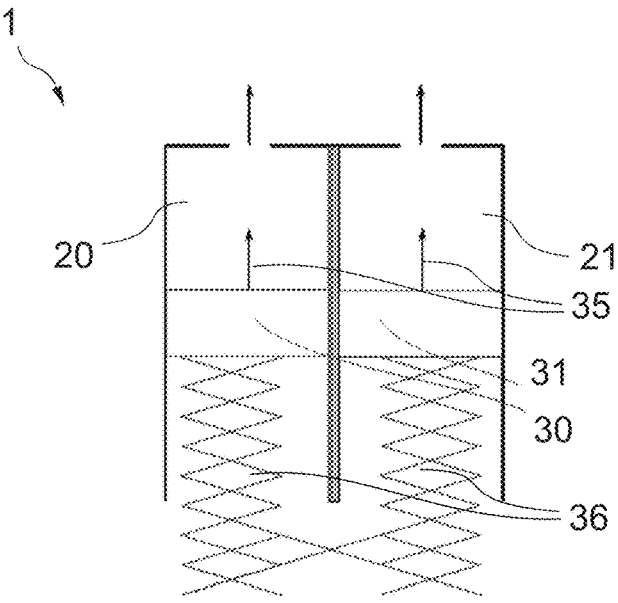
FIG. 15 shows the device according to the invention with two force transmission elements.

FIG. 15 shows an implementation of the device 1 in which the thrust of the pistons 30, 31 is realized mechanically, wherein a force transmission element 36 is connected to a respective piston so that both pistons 30, 31 can be displaced synchronously by introducing forces through the force transmission elements 36.

Figure 16:
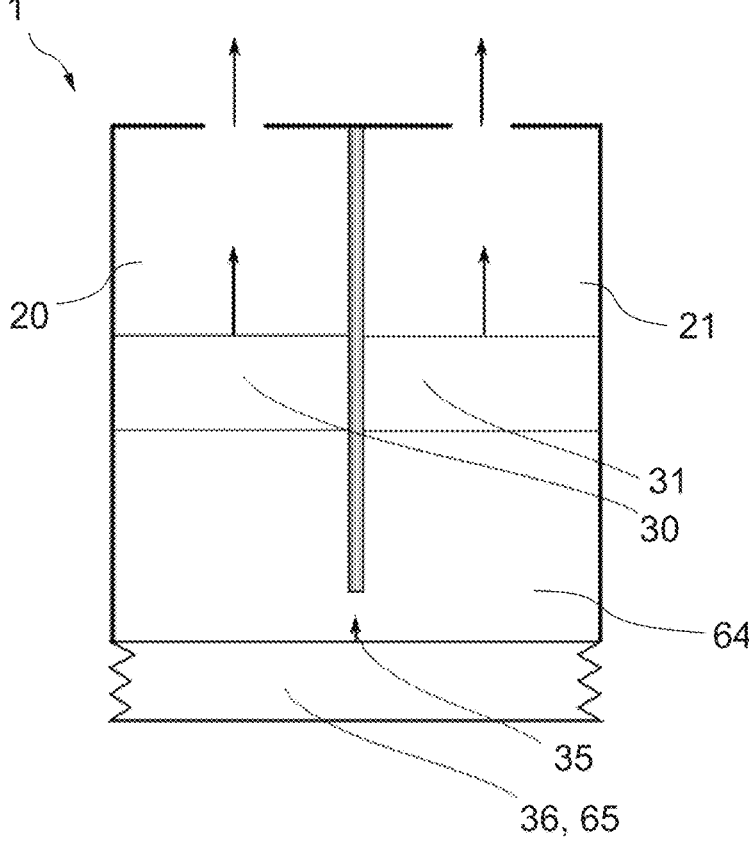
FIG. 16 shows the device according to the invention with the pressure chamber.

FIG. 16 shows an implementation of the device 1 in which the thrust of the pistons 35 is realized by the effect of a gas pressure on the pistons 30, 31. In this case, a common pressure chamber 64 is assigned to the two pistons 30, 31 shown, as well as a second pump 65, which is set up to generate an overpressure in the pressure chamber 64, so that the two pistons 30, 31 can be displaced simultaneously or synchronously due to the overpressure.

Figure 17:
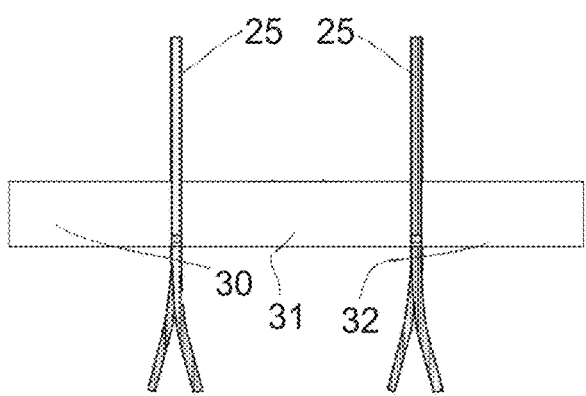
FIG. 17 shows three pistons connected to one another during the cutting process.

FIG. 17 shows an implementation of the device 1 with three pistons 30, 31, 32 during the cutting process, wherein the coupling of the pistons is implemented here exemplarily in that the pistons 30, 31, 32 are designed as one continuous piston. A partition 25 is arranged between two of the three pistons 30,31,32, respectively.

Figure 18:
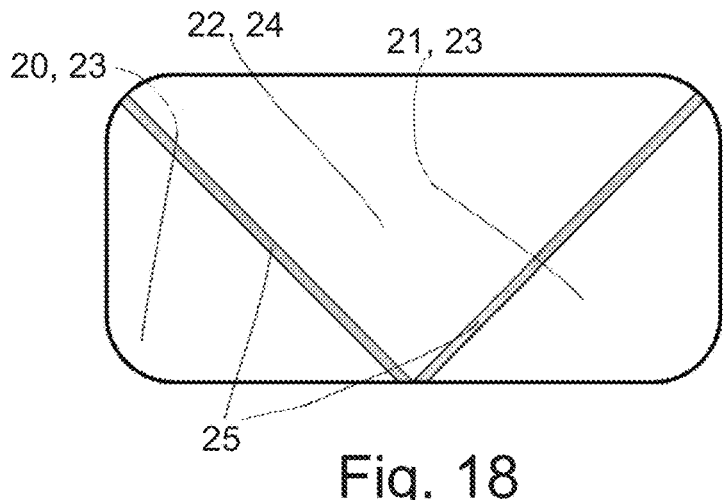
FIG. 18 shows three reservoirs with triangular cross-section.

FIG. 18 shows a first reservoir 20, a second reservoir 21 and a third reservoir 22, and that the partition walls 25 do not necessarily need to be arranged parallel to each other. In particular, at least one reservoir 20,21,22 may fully or partially enclose at least one other reservoir, as shown in FIG. 18. This is advantageous in order to protect the fluid in the inner reservoir, particularly a fluid containing $H_2O_2$, from light irradiation and consequent decomposition of $H_2O_2$, for example by adding a respective dye to the fluid in an outer reservoir, thereby reducing the translucency of the fluid in the outer reservoir and consequently the light irradiation on the fluid in the inner reservoir.

Figure 19:
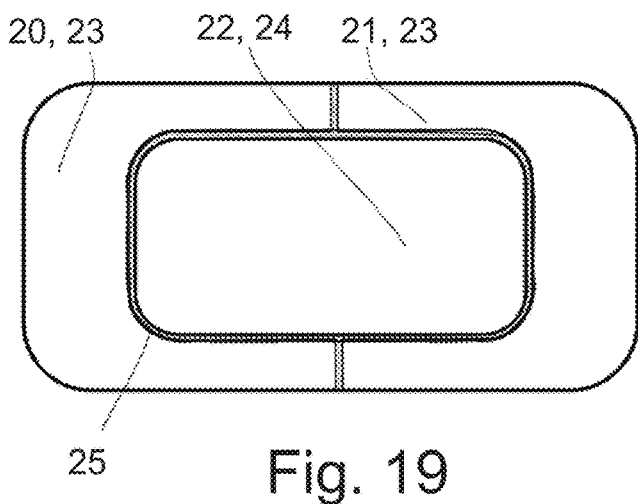
FIG. 19 shows three reservoirs with a central arrangement of a reservoir.

FIG. 19 shows an exemplary arrangement of three reservoirs 20,21,22 of the device 1, wherein the two outer reservoirs 23 surround the inner reservoir 24, also to reduce or avoid light irradiation into the liquid in the inner reservoir 24.

EXAMPLES

Disinfection Process without Retarding Solvent

The pH-dependent rate constant $k=k_0$ can be calculated as follows:

$$k_0 = k^* \frac{[H_3O^+]^2}{\left(K_{S,H_3O_2^+} + [H_3O^+]\right)\left(K_{S,HNO_2} + [H_3O^+]\right)} \text{ with} \tag{40}$$

$$k^* = 3,56 \cdot 10^{14} \exp\left(-\frac{E_A}{RT}\right) M^{-1} s^{-1} \tag{50}$$

$$K_{S,HNO_2} = 5,13 \times 10^{-4} \tag{60}$$

$$K_{S,H_3O_2^+} = 2 \times 10^{-2} \tag{70}$$

and the unitless quantity $$[H_3O^+] = 10^{-PH} \tag{80}$$

with an effective activation energy $E_A$=70 KJ/mol and the temperature T.

As an example, by solving the differential equations resulting from (2) for the concentrations $[H_2O_2]$ and $[NO_2]$ at the same starting concentrations at time to of $[H_2O_2]_0$= $[NO_2]_0$=20 mM as well as a pH value of 3.2 and a temperature of 37° C., the concentration curves shown in FIG. 1 above are obtained. In FIG. 1 below, the reaction rate is given according to equation (3). The filled region in FIG. 1 below illustrates the integral (1) with $t_0$=15 s and $t_1$=75 s, wherein in this case an efficacy parameter of W (15 s to 75 s)=3.8 mM is obtained. As can be easily seen from FIG. 1 below, the agent is more effective during the distribution step than during the actual exposure time: calculating the integral (1) during the processing time, i.e. with $t_0$=0 s and $t_1$=15 s, gives an efficacy parameter of W (0 s to 15 s)=14.7 mM. Thus, a large part of the effective potential is not utilized. The duration of the distribution step depends on the respective process and cannot be freely selected or arbitrarily shortened. For example, a distribution time of 30 s is common for hygienic hand disinfection.

Experiments Performed
Influence of Isopropanol on the Rate Constant

Figure 2:
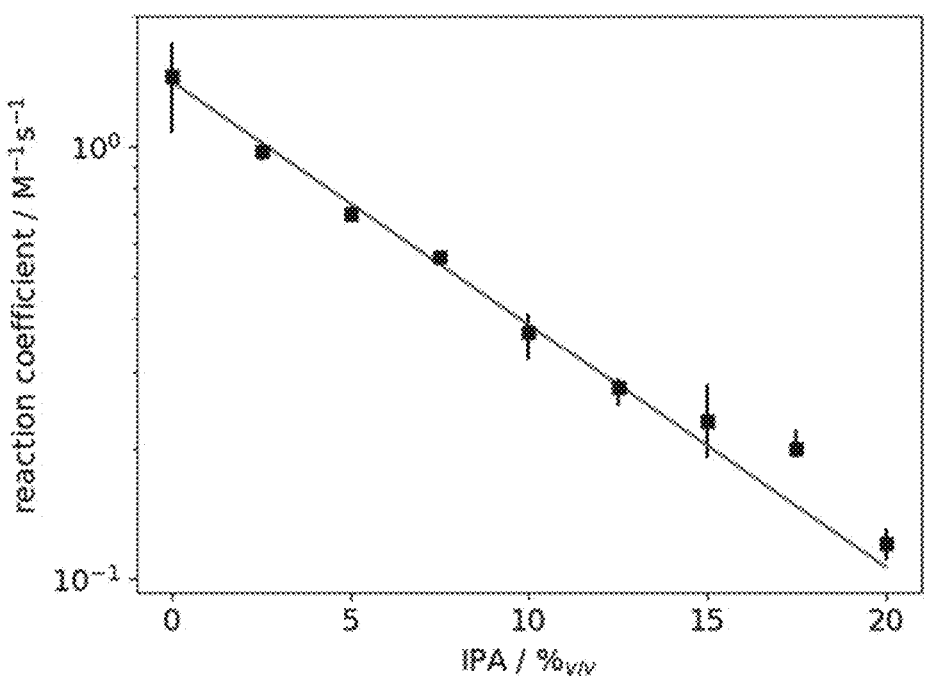
FIG. 2 shows the influence of isopropanol concentration IPA on the reaction coefficient of reaction (2) at 20° C.

FIG. 2 shows the influence of isopropanol (IPA) added to the active solutions on the rate constant (40) at a temperature of 20° C. The measurement of the reaction constant was carried out here using UV spectroscopy, wherein the decrease in $NO_2^-$ concentration was quantified to determine the reaction rate. As shown in FIG. 2, the reaction (2) can be effectively slowed down by adding isopropanol. The influence of the isopropanol concentration on the reaction rate of reaction (2) can be taken into account by multiplying the rate constant $k_0$ by a factor dependent on the isopropanol concentration IPA (given in volume percent) according to $$k = k_0 \times \exp(-0,129 \times IPA) \tag{90}$$

Temporal Change of Isopropanol Concentration on Surfaces

If a solution of water and a solvent with a higher vapor pressure than water is applied to a surface, the solvent evaporates more quickly, reducing its proportion in the solution. The following experiment was performed for this purpose: A metal plate with an area of 567 cm$^2$ was heated to a temperature of $(37\pm2)°$ C. 3 mL of an isopropanol solution was spread on the plate. After waiting for 30 s or 60 s, the liquid remaining on the surface was collected in a vessel and the density of the liquid was determined. For this purpose, the weight of 100 μL of the collected liquid was measured. From the data presented in Chu, Kwang-Yu, and A. Ralph Thompson. Journal of chemical and engineering data 7.3 (1962): 358-360 regarding the concentration dependence of the density of isopropanol solutions, the isopropanol concentration of the collected liquid was determined. Furthermore, for verification of the method, the density of the isopropanol solution was determined before it was applied to the metal plate (designated "0 s" in FIG. 3) as well as from distilled water (H$_2$O dest). The selected temperature and area are particularly relevant as a model for hand disinfection. In this case, the active solution is also heated by body heat and frictional heat when hand disinfection is carried out as prescribed. In addition, an even greater surface-to-volume ratio of the distributed active solution occurs during hand disinfection due to the surface properties of the skin.

Temporal Change of the Reaction Rate (3) on Surfaces

Figures 3, 4:
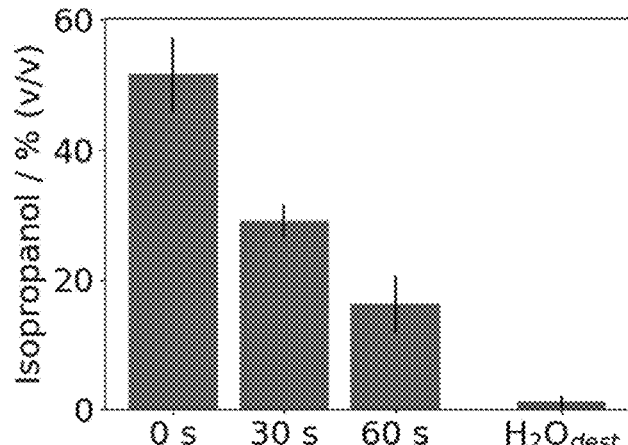
FIG. 3 shows the isopropanol concentration of an initially 50% isopropanol solution after 0 s, 30 s and 60 s on a metal plate heated to 37° C. The isopropanol concentration of the isopropanol solution is shown in FIG. 3.
FIG. 4 shows the assumed concentration curve of isopropanol (top), the calculated concentration curve of $H_2O_2$ and $NO_2^-$ (middle) and the reaction rate (bottom) respective to equation (3) with rate constant (9) and initial concentrations $[H_2O_2]_0=[NO_2]_0=20$ mM as well as a pH value of 3.2 and a temperature of 37° C. The filled region illustrates the integral over the exposure time from $t_1=15$ s to $t_2=75$ s.

The concentration dependence (90) together with the time variation of the isopropanol concentration shown in FIG. 3 can be exploited to retard the progress of the reaction (2). FIG. 4 (top) shows the time course of an assumed isopropanol concentration during surface disinfection with a solution of H$_2$O$_2$ and NO$_2$. FIG. 4 (middle) shows the concentrations of [H$_2$O$_2$] and [NO$_2$] resulting from equations (1) and (90), wherein the initial concentrations are [H$_2$O$_2$]$_0$= [NO$_2$]$_0$=20 mM, pH value 3.2 and temperature 37° C. Thus, with the exception of the isopropanol concentration, the same conditions were chosen as in the calculation shown in FIG. 1. However, with the reaction time starting at t$_1$=15 s and ending at t$_2$=75 s, the efficacy parameter here is WIPA (15 s to 45 s)=13.1 mM due to the retarded reaction. This is 9.3 mM higher compared to the value of W (15 s to 45 s)=3.8 mM obtained without the use of IPA. This demonstrates that adding a solvent that decreases the reaction rate of reaction (2) produces a more effective disinfectant.

Figure 5:
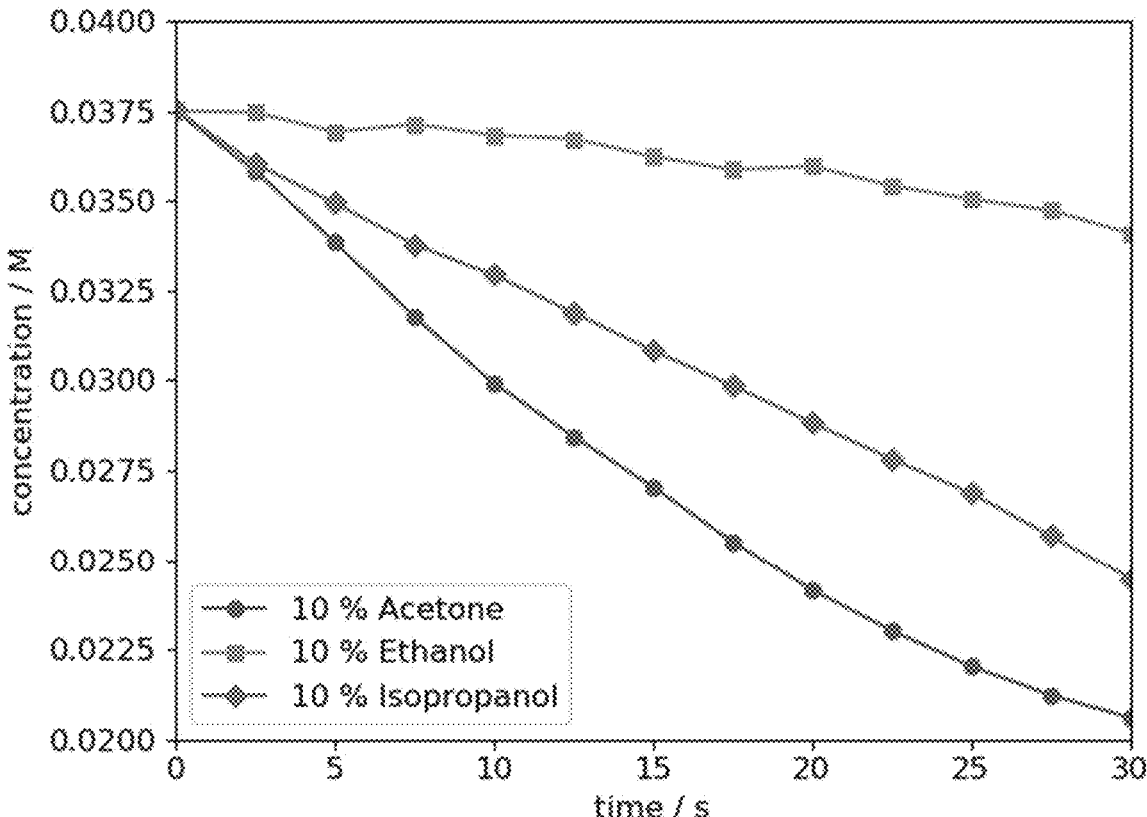
FIG. 5 shows the concentration curve of nitrite when 10% ethanol, acetone or isopropanol is added.

FIG. 5 shows the influence of different solvents on the reaction rate of reaction 2. The measurements were carried out using UV spectroscopy with an absorption length of 1 cm and at a wavelength of 332 nm.

Microbiological Examinations

In order to verify the retarded microbiological effect when using a stopping solution, the effect of the active solution on spores of the species *Bacillus atrophaeus* was investigated in two experiments.

In the first experiment, 10 μL of a spore solution (containing spores of the bacterium of species *Bacillus atrophaeus*) was placed in a reaction vessel. Then, 495 μL of a 50 mM NaNO$_2$ solution was added, followed by 495 μL of a 50 mM H$_2$O$_2$ solution to obtain an active solution. Here, the NaNO$_2$ solution and the H$_2$O$_2$ solution respectively contained the same concentration of isopropanol selected from 0%, 5%, 10%, 15% or 20%, wherein the percentages refer to percent by volume. In addition, the H$_2$O$_2$ solution was acidified using 25 mM H$_3$PO$_4$. The reaction was stopped after an incubation time of 60 s by dilution in a neutralization solution and then plated out on agar. After an incubation period of 24 h, the colony forming units were quantified on the respective agar plate.

Figure 6:
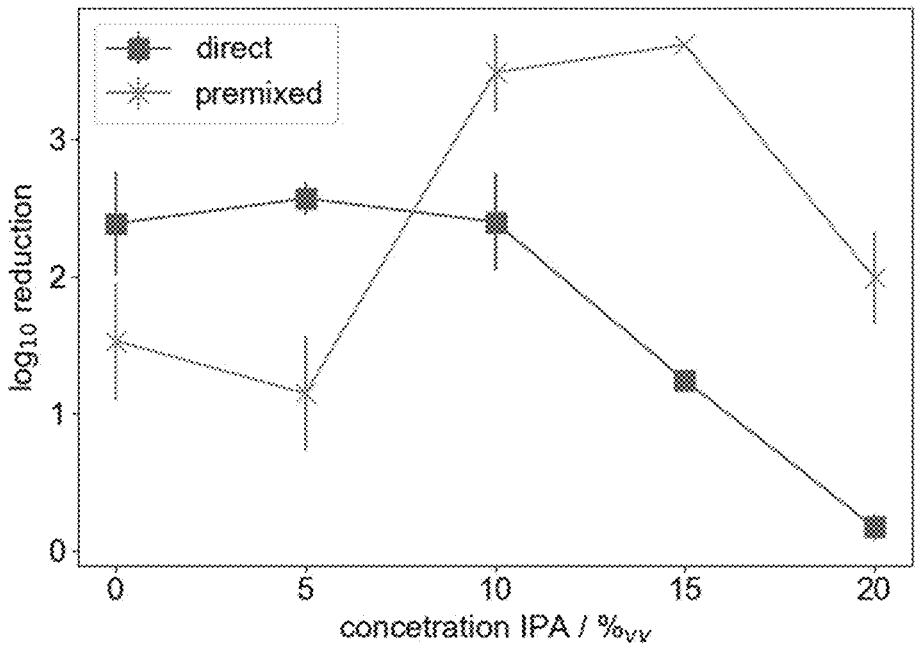
FIG. 6 shows the inactivation of spores of *Bacillus atrophaeus* in the experiment without preceding mixing of the educts (direct) as well as with preceding mixing of the educts (premixed) (see section "Microbiological examinations").

The results of this test are shown in FIG. 6 (measurement series "direct"). The specified "log 10 reduction" is the negative decadic logarithm of the determined concentration of colony-forming units after application of the respective active solution in relation to the determined bacteria concentration in a negative control. As can be seen from the data, the addition of isopropanol leads to a deterioration in the effect of the respective active solution. In the light of the preceding investigations, it is clear that the deterioration of the effect is due to a reduction in the reaction rate, for example, in accordance with equation (90).

In the second experiment, 10 μL of a spore solution (*B. atrophaseus*) was introduced analogously to the first experiment. In a separate reaction vessel, 1 mL of a 75 mM NaNO$_2$ solution was added and reacted with 1 mL of a 75 mM H$_2$O$_2$ solution to obtain an active solution. After 15 s of reaction time, 990 μL of this active solution was added to the spore solution. Analogous to the first experiment, the NaNO$_2$ solution and the H$_2$O$_2$ solution respectively contained the same concentration of isopropanol selected from 0%, 5%, 10%, 15% or 20%. In addition, the H$_2$O$_2$ solution was acidified using 37.5 mM H$_3$PO$_4$. The higher concentrations of the educts compared to the first experiment were chosen here to approximately compensate for the loss of these educts during the 15 s reaction time. Analogous to the first experiment, the solution was diluted in neutralization solution after 60 s of reaction time and plated out.

The results of this experiment are shown in FIG. 6 ("premixed" series of measurements). As can be seen from this, the addition of isopropanol in this experiment leads to an improvement in the sporicidal effect for isopropanol concentrations of up to 15%—the trend is thus contrary to the observation in the first experiment. However, this is also due to the fact that the isopropanol acts as a stopping solution here. As a result, the reaction proceeds more slowly during the 15 s reaction time, so that even more educts are available during the exposure time. At an isopropanol concentration of 20%, the reaction in this experiment is already slowed down to such an extent that fewer educts (compared with the 15% experiment) are converted during the exposure time and the effect is therefore inferior.

Example of Determining the Minimum Solvent Concentration that can be Used

Definitions

The total process time is the distribution time+drying time. The distribution time ends at time t$_1$.

Drying time=time until wetted surface is completely dry, ends at time t$_2$.

$$c_{t_1}^{min}(x) = \min\!\left(c_{H_2O_2}(x, t = t_1),\, c_{NO_2^-}(x,\ t = t_1)\right),$$

where x is the concentration of the stopping agent in volume percent relative to the volume of the active solution at time t=t$_0$.

The function min (a,b) is equal to a if a<b, b if b≤a.

$$c_{t_1}^{min}(0)$$

refers to an active solution without stopping agent.

$$c_{t_1}^{min}$$

corresponds to the maximum achievable efficacy $$WW = \int_{t_1}^{\infty} k \cdot [\mathrm{H_2O_2}] \cdot [\mathrm{NO_2^-}] dt,$$

wherein k denotes the rate constant of the reaction between $\mathrm{H_2O_2}$ and $\mathrm{NO_2}$.

It is advantageous if the total process time is as short as possible. It is also advantageous if the efficacy is as high as possible during the drying time. The drying time can always be shortened by adding an alcohol with a lower boiling temperature than water.

In addition, the efficacy is increased by adding alcohol in the drying time. The following points must be taken into account when designing the alcohol concentration:

a) Minimum alcohol addition:

The alcohol concentration must be chosen so that the condition $$\frac{c_{t_1}^{min}(x)}{c_{t_1}^{min}(0)} > 1, 2, \qquad (100)$$

is satisfied.

b) Maximum alcohol addition:

Too high an alcohol concentration can lead to unwanted changes in the treated surfaces or, in the case of application to the skin, to skin irritation, so the alcohol concentration should be chosen as low as possible. In particular, the alcohol concentration should be less than 90%, in particular less than 60%, in particular less than 40%.

Figure 7:
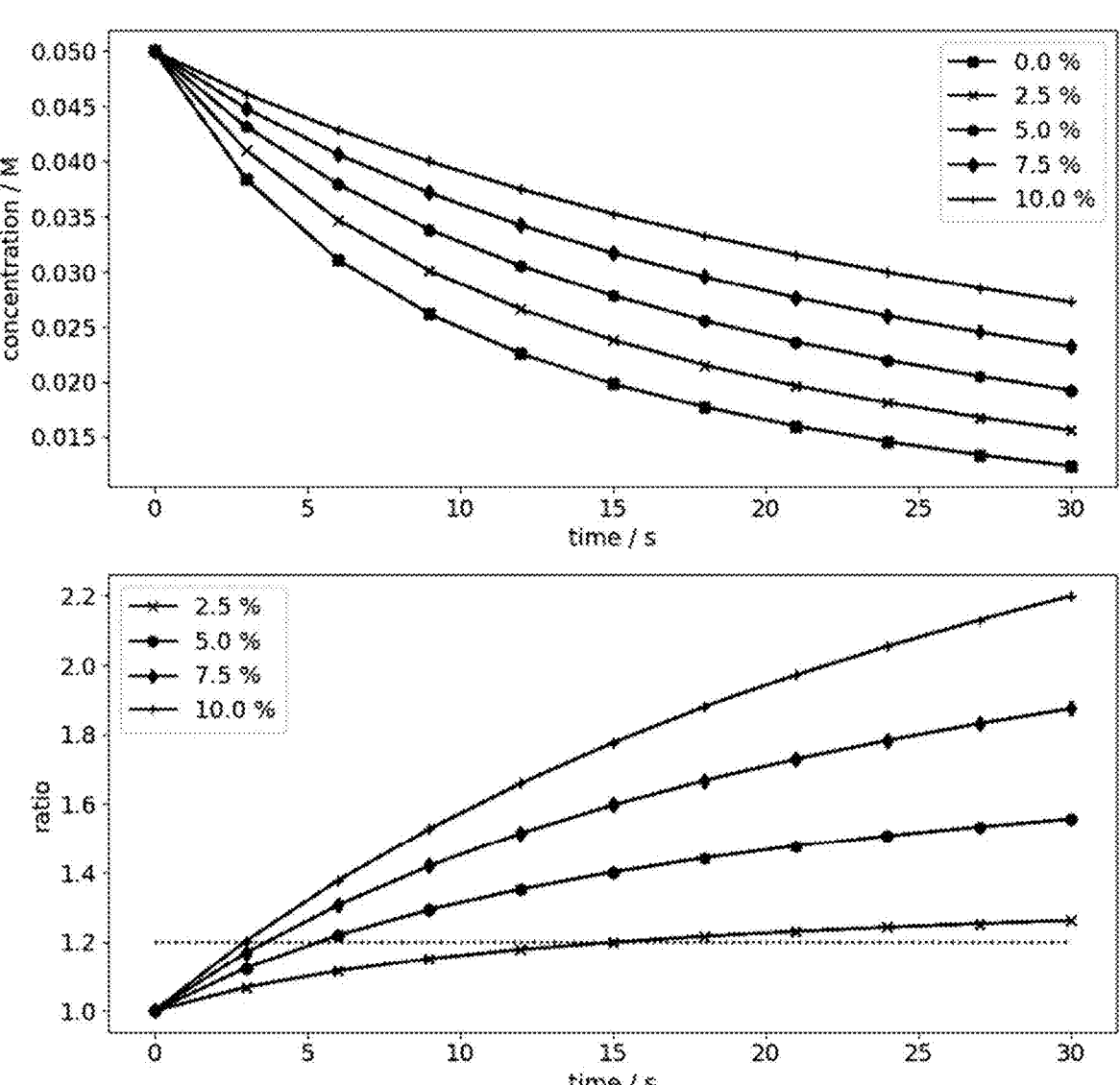
FIG. 7 shows the time course of the concentrations $[H_2O_2]$ and $[NO_2]$ at initial concentrations $[H_2O_2]_0=[NO_2]_0=50$ mM, a pH value of 3.2 at 20° C. (top) as well as the ratio $n_{r1}^{min}(x)/n_{r1}^{min}(0)$ (bottom). The dashed line indicates the ratio $n_{r1}^{min}(x)/n_{r1}^{min}(0)=1,2$.

FIG. 7 (top) shows an example of the concentration curve for $\mathrm{NO_2^-}$ and $\mathrm{H_2O_2}$ for admixtures of 0, 2.5, 5.0, 7.5 and 10.0% isopropanol. FIG. 7 (bottom) shows the ratios $$n_{t_1}^{min}(x) \big/ n_{t_1}^{min}(0).$$

In addition, the dashed line indicates the required 20% improvement, so that the region to be selected according to the invention can be read off from equation (X).

Determination of the Minimum Applicable Solvent Concentration

A disinfectant is required which permits a distribution time of at least 15 s, comprises a pH value of 3.2 and wherein isopropanol is used as the retarding solvent. The following steps are to be carried out:

1. The concentration of $\mathrm{H_2O_2}$ and $\mathrm{NO_2^-}$ are to be measured time-resolved at a given pH value after mixing the components for different isopropanol concentrations. This can be carried our, for example, using UV spectroscopy as indicated in PCT/EP2019/062897 and above (see FIG. 7 above).

2. For the selected isopropanol concentrations x, the ratio $$n_{t_1}^{min}(x) \big/ n_{t_1}^{min}(0)$$

is to be determined (see FIG. 7 below) and the condition $$n_{t_1}^{min}(x) \big/ n_{t_1}^{min}(0) > 1, 2$$

is to be verified. In this example, an isopropanol concentration of 2.5% is the minimum solvent concentration that can be used.

For other solvents and pH values, analogous steps must be taken.

Literature List:

Zhu, Ling, Christopher Gunn, and Joseph S. Beckman. "Bactericidal activity of peroxynitrite." Archives of biochemistry and biophysics 298.2 (1992): 452-457.

Chu, Kwang-Yu, and A. Ralph Thompson. "Densities and Refractive Indices of Alcohol-Water Solutions of n-Propyl, Isopropyl, and Methyl Alcohols." Journal of chemical and engineering data 7.3 (1962): 358-360.

The invention claimed is:

1. A method for disinfecting a surface, comprising:

mixing $\mathrm{H_2O_2}$, $\mathrm{NO_2}^-$, and at least one stopping agent at time $t_0$ to obtain an active solution, wherein the initial concentration of $\mathrm{NO_2}^-$ at time $t_0$, $[\mathrm{NO_2}^-]_0$, is between 15 and 300 mM and wherein the stopping agent is a solvent having a boiling temperature below 100° C., providing the active solution to the surface, wherein the at least one stopping agent reduces the reaction rate of $\mathrm{H_2O_2}$ and $\mathrm{NO_2}^-$, thereby retarding formation of peroxynitrous acid, wherein the retarding effect of the stopping agent decreases as soon as the concentration of the stopping agent is reduced; and evaporating the at least one stopping agent, thereby allowing the reactants to form peroxynitrous acid and disinfect the surface.

2. The method of claim 1, wherein the stopping agent is selected from an alcohol, a ketone and an ester.

3. The method according to claim 1, wherein the active solution is distributed on a surface to be disinfected until complete wetting at time $t_1$.

4. The method according to claim 1, wherein the time period between $t_0$ and $t_1$ is at least 5 seconds.

5. The method according to claim 1, wherein the active solution acts until time $t_2$ to obtain a disinfected surface.

6. The method according to claim 1, wherein the minimum concentration of the stopping agent in the active solution at time to is at least 2.5% (v/v) and/or the maximum concentration of the stopping agent in the active solution is <90% (v/v).

7. The method according to claim 1, wherein the pH-value of the active solution at time to is between 1 and 7.

8. The method according to claim 1, wherein the initial concentration $[\mathrm{H_2O_2}]_0$ at time to is between 1 mM and 1000 mM.

9. The method of claim 1, wherein the stopping agent is selected from methanol, ethanol, isopropanol, acetone, ethyl acetate and n-propanol.

10. The method of claim 1, wherein the stopping agent is selected from methanol, ethanol, isopropanol and acetone.

11. The method according to claim 1, wherein the time period between to and $t_1$ is at least 10 seconds.

12. The method according to claim 1, wherein the time period between to and $t_1$ is at least 15 seconds.

13. The method according to claim 1, wherein the pH-value of the active solution at time to is between 3 and 5.

14. The method according to claim 1, wherein the minimum concentration of the stopping agent in the active solution at time to is at least 2.5% (v/v) and/or the maximum concentration of the stopping agent in the active solution is <40% (v/v).

15. The method according to claim 1, wherein the initial concentration $[H_2O_2]_0$ at time to is between 10 mM and 500 mM.

16. The method according to claim 1, wherein the initial concentration $[H_2O_2]_0$ at time to is between 15 and 300 mM.

* * * * *